United States Patent [19]

Goldberg et al.

[11] Patent Number: 5,152,777
[45] Date of Patent: Oct. 6, 1992

[54] DEVICE AND METHOD FOR PROVIDING PROTECTION FROM EMBOLI AND PREVENTING OCCULSION OF BLOOD VESSELS

[75] Inventors: Edward M. Goldberg, Glencoe; Lev Melinyshyn, Mt. Prospect; Alexander Poloyko, Morton Grove, all of Ill.

[73] Assignee: Uresil Corporation, Skokie, Ill.

[21] Appl. No.: 301,656

[22] Filed: Jan. 25, 1989

[51] Int. Cl.$^5$ ............................................. A61B 17/00
[52] U.S. Cl. ................................................... 606/200
[58] Field of Search .............. 606/200, 198, 194, 195, 606/191, 127

[56] References Cited

U.S. PATENT DOCUMENTS

| | | |
|---|---|---|
| 3,540,431 | 11/1970 | Mobin-Uddin ................ 606/200 X |
| 3,635,223 | 1/1972 | Klieman ......................... 606/200 X |
| 3,923,065 | 12/1975 | Nozick et al. .................. 606/200 X |
| 3,996,938 | 12/1976 | Clark .............................. 606/200 |
| 4,655,771 | 4/1987 | Wallsten ........................ 604/281 X |
| 4,669,464 | 6/1987 | Sulepov ......................... 606/200 X |
| 4,723,549 | 2/1988 | Wholey et al. ................. 606/194 |
| 4,727,873 | 3/1988 | Mobin-Uddin ................. 606/200 |
| 4,873,978 | 10/1989 | Ginsburg ....................... 606/200 X |

Primary Examiner—Michael H. Thaler
Attorney, Agent, or Firm—Laff, Whitesel, Conte & Saret

[57] ABSTRACT

An apparatus and method for providing protection from emboli and prevention of occlusion in blood vessels entailing the use of a temporarily emplaced, complaint and conformable trap which may be removed when medically necessary and which will not damage the architecture of the blood vessel.

23 Claims, 3 Drawing Sheets

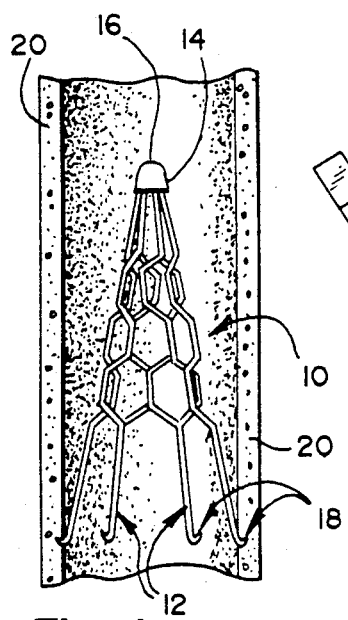
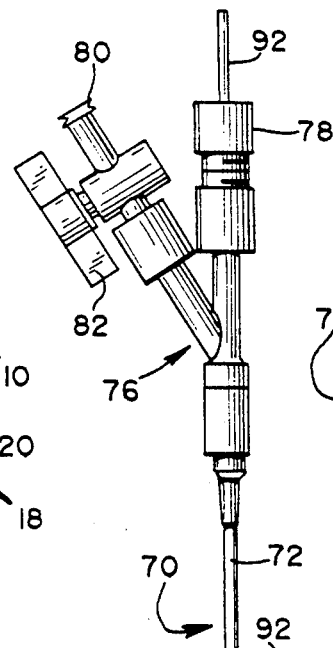
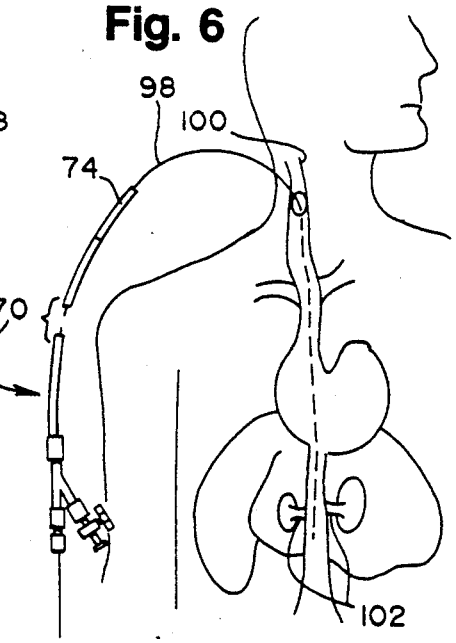
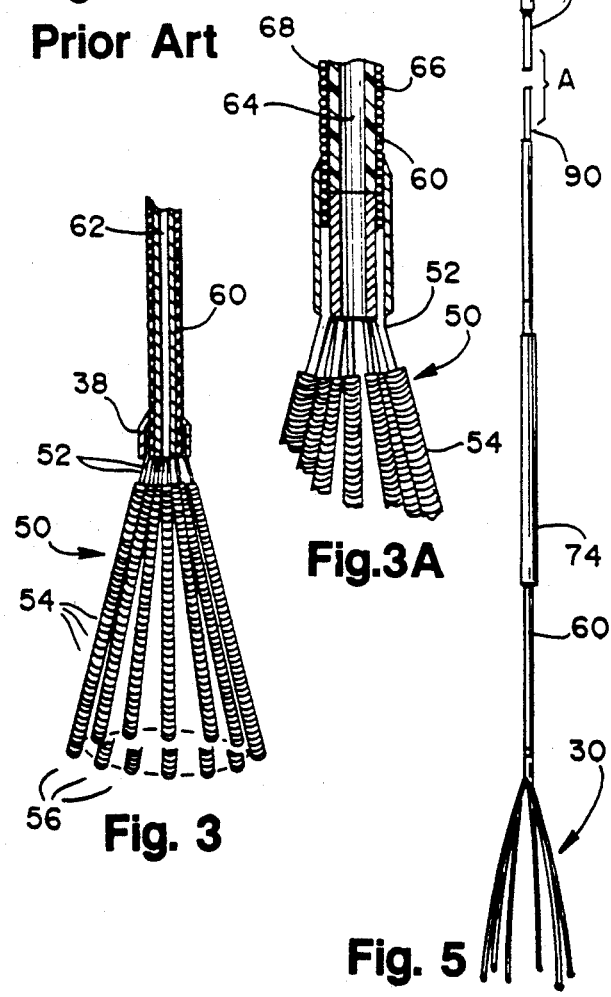
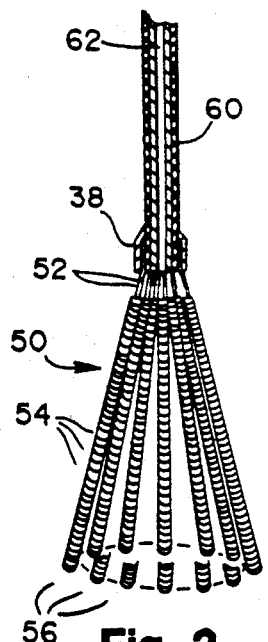
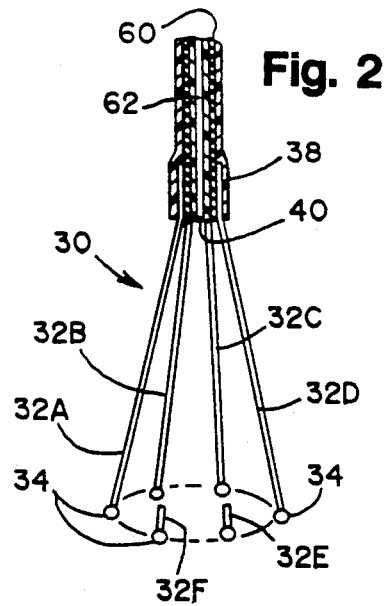
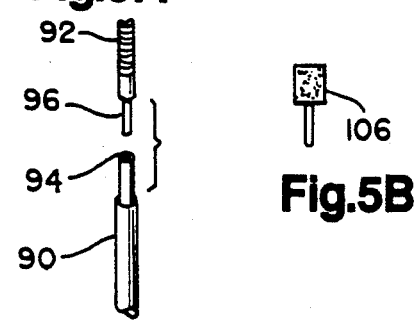

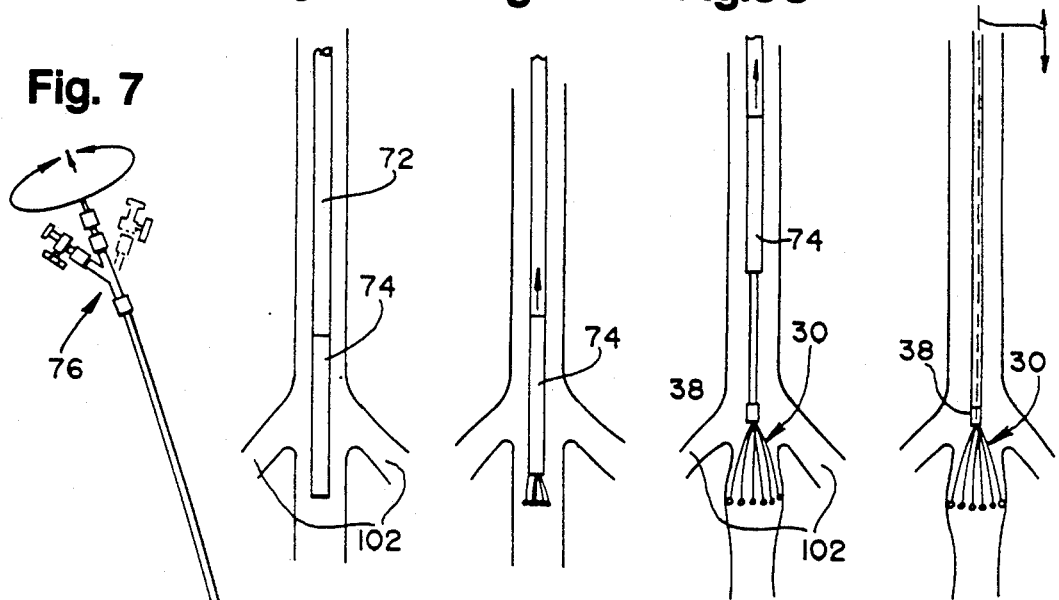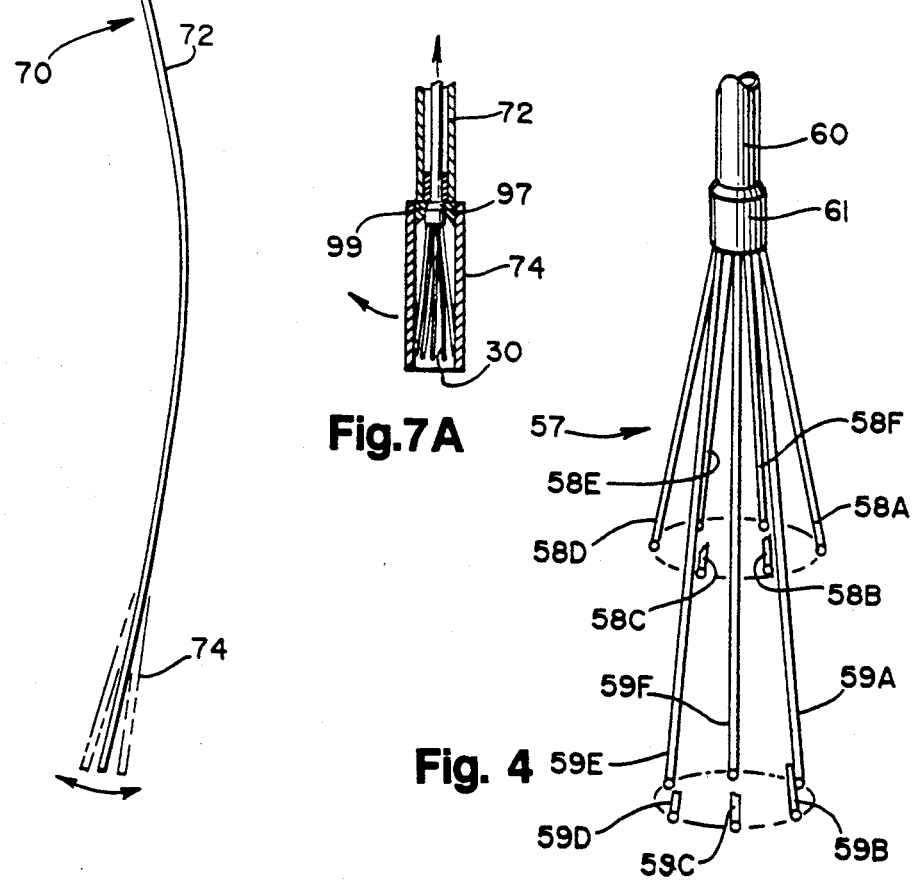

DEVICE AND METHOD FOR PROVIDING PROTECTION FROM EMBOLI AND PREVENTING OCCULSION OF BLOOD VESSELS

BACKGROUND OF THE INVENTION

This invention relates generally to devices and methods for trapping blood clots and controlling embolization and thrombosis in blood vessels. More particularly, this invention relates to an apparatus and a method for providing protection from emboli and thrombi and for preventing occlusion in a blood vessel using a unique new trap for capturing emboli passing through the vessel. The trap includes an obturated below stem which maintains the trap in its desired location for as long as required, allows for the introduction of fluids to the region of the trap for purposes of venography and lysis of trapped emboli or thrombi, and permits the trap to be withdrawn when medically appropriate without releasing emboli or newly formed thrombi into the bloodstream.

The presence of emboli within the body's circulatory system presents significant health hazards from potential acute venous thrombosis and chronic deep vein thrombosis. Acute venous thrombosis can lead to pulmonary embolism, when an embolus travels into the plumonary arteries.

Surgical approaches to control both chronic deep vein thrombosis and acute venous thrombosis have been used for many years. Currently, the most widespread approach is treatment with systemic and oral anticoagulants, such as heparin and coumadin and with thrombolytic agents such as TPA, urokinase and streptokinase. The initial treatment of pulmonary embolism is similar.

Unfortunately, such chemical therapy is ineffective or inappropriate in some patients. Since most pulmonary emboli originate in veins of the lower limbs, pelvis or inferior vena cava, life-threatening pulmonary emboli can be prevented from reaching the lungs by mechanically interrupting the inferior vena cava to trap emboli, preferably proximally to the heart.

Indications for creating or introducing traps in the inferior vena cava include:

a) Pulmonary embolism in patients with a high risk of internal bleeding, including those having recent trauma, surgery, cerebral hemorrhage or peptic ulcer disease who are not amenable to anticoagulant or thrombolytic therapy.

b) Recurrent pulmonary emboli notwithstanding anticoagulant therapy.

c) Patients showing large free-floating thrombi in the iliofemoral veins or inferior vena cava identified with venography.

d) As prophylaxis against pulmonary emboli in older patients with high-risk conditions.

e) Disseminated thrombosis and profound thrombocytopenia in patients displaying heparin sensitivity.

f) Prevention of recurrent pulmonary emboli after pulmonary thrombolectomy.

Techniques for mechanical interruption of the vena cava have included suturing grids across the inferior vena cava and applying external clips to the vessel to produce parallel, reduced orifices. Unfortunately, these procedures require general anesthesia and laparotomy subjecting patients who are already seriously ill to increased danger of post-operative complications and further may cause occlusion of the vena cava with all of its associated sequelae.

In 1967–68, Eichelter and Schenk described an umbrella-like device which they introduced under local anesthesia into the femoral vein of dogs to filter emboli. Eichelter, P., Schenk, W. G., Jr.: "A New Experimental Approach to Prophylaxis of Pulmonary Embolism", Rev Surg 24:455–456 (Nov-Dec) 1967; Eichelter, P., Schenk, W. G., Jr.: "Prophylaxis of Pulmonary Embolism", Arch Surg 97: 348–356 August 1968. The Eichelter/Schenk device was constructed by making longitudinal incisions circumferentially around a segment of a polyethylene tube, placing a tube of smaller diameter inside the larger tube and flaring the end protruding beyond the linear incisions. Light traction of the inner tube while holding the outer tube stable produced an umbrella-like structure. Unfortunately, this structure included numerous apertures for trapping stagnant blood and thereby promoting highly undesirable thrombosis and potential embolization.

Eichelter/Schenk made a small incision in the right femoral vein of the groins of the dogs used in the tests, with the distal portion of the catheter tied into the femoral vein and the device open at a point lying distal to the renal veins. After a number of weeks, the device was collapsed and removed through a small incision. The embolization of trapped or attached emboli upon removal of the Eichelter/Schenk device precluded use of this device in humans. No further study of application of this device has been reported, as far as the present inventors can ascertain.

A permanent implantable vena cava filter was developed by Mobin-Uddin in 1969, and described in U.S. Pat. No. 3,540,431. This filter is intended to be introduced through an incision in the jugular vein. The Mobin-Uddin filter is an umbrella-like structure having expanding ribs carrying sharpened points at their divergent ends which impale the walls of the blood vessel when the filter is positioned at the desired location and permitted to expand into its operative structure. The Mobin-Uddin filter has a high occlusion rate and is therefore not widely used. Furthermore, the sharpened points create the possibility of retroperitoneal bleeding from perforations in the vessel wall. Indicated heparin treatment is typically withheld for 12 hours after insertion to minimize the danger of this complication. Finally, even if initially properly implanted, these filters can come loose and migrate to either ineffective or dangerous and life-threatening locations in the vascular system.

The development of the Mobin-Uddin device lead to the introduction of a series of other permanently implantable filters, including the currently most widely used vena cava filter, the Kimray-Greenfield filter, described in U.S. Pat. No. 3,952,747. This filter, depicted at 10 in FIG. 1, comprises a plurality of wire legs 12 extending in a generally conical array from a nose 14 having a port 16. While the Kimray-Greenfield filter is structurally different from the Mobin-Uddin device, it also includes sharpened hooks 18 to permanently anchor the filter by impaling the hooks in the blood vessel walls 20 giving rise to the associated danger of retroperitoneal bleeding. As in the case of the Mobin-Uddin device, the Kimray-Greenfield filter can come loose and migrate to either ineffective or dangerous and life-threatening locations in the vascular system. Additionally, port 14 can trap and hold blood, promoting undesirable thrombosis and potential embolization.

The Kimray-Greenfield filter is difficult to load before emplacement due to the interference of the hooks with each other when the filter is folded into the ejector used in the emplacement. It is also difficult to emplace since it is a "one-shot" system—once the filter is ejected and implanted it cannot be moved. The Kimray-Greenfield is subject to premature or inadvartent ejection during emplacement, resulting in permanent placement at an inappropriate location and often requiring the placement of an additional filter at the desired location.

Another of the vessel wall anchoring devices is the Amplatz filter, which is described in "Amplatz Retrievable Vena Cava Filter," *Seminars In Interventional Radiology*, Vol. 3, No. 3, September 1986, by M. D. Darcy, D. W. Hunter, G. B. Lund, and J. F. Cardella. This filter is spider shaped, with six prongs each having a central wire that impales the vena cava wall, again raising the specter of retroperitoneal bleeding from perforations in the vessel wall. Although this device is described as being "retrievable", retrieval is both difficult and problematic.

The Amplatz filter is designed to be withdrawn through the femoral vein by ensnaring a hook at the caudal end of the filter, a difficult and oftentimes unsuccessful procedure. Furthermore, and perhaps more importantly, retrieval must be performed within the first several weeks after emplacement since the hooks become increasingly entrapped in the vessel walls due to encroaching fibrosis, raising an unacceptable danger of damage to the vessel architecture on removal after several weeks in place.

There are a multitude of problems associated with current vena cava filters designed to be fixed in place by way of hooks which impale caval or other blood vessel walls. A thrombus at the implant site can prevent or complicate engagement of the hooks. Even if initially properly implanted, the filters sometimes come loose and migrate to either ineffective or dangerous and life-threatening locations in the vascular system. Perforation of the vessel wall by the filter hooks occurs, with the danger of damage to the vessel wall, providing new sites for emboli formation, and a danger of puncture, causing internal bleeding and clinical sequela. Some of the filters are particularly subject to occlusion. Many tilt after or during emplacement permitting large, dangerous emboli to escape the filter into the bloodstream. The emplacement procedure for most current filters is cumbersome and requires large diameter ejector devices which are difficult to maneuver through blood vessels particularly when variations in the vessel architecture are encountered.

Finally, once the thrombotic condition sought to be treated is resolved—typically in about six weeks to six months—it is desirable to remove the filter to open up complete flow through the vessel and remove at best an unwelcome foreign body. Since the present filters are for all intents and purposes fixed permanently in place, this is not presently possible. Thus, the propriety of the use of the current devices is questionable, particularly in younger patients whose life expectancy is substantially great and the clinical need for the filter may be short. A great number of patients require only temporary safety from pulmonary embolization and prophylactic heparin may be contraindicated or otherwise unsafe particularly where surgery is contemplated.

The present invention solves the problems inherent in the prior art devices and methods by providing a system in which a quick and safe, positive, temporary emplacement of a compliant, conformable emboli trap is accomplished without impaling blood vessel walls or causing any of the other problems associated with prior art devices.

SUMMARY OF THE INVENTION

It is therefore an object of the present invention to provide an apparatus which can be quickly, safely and temporarily emplaced within a blood vessel for the purpose of trapping emboli passing through the vessel.

Yet another object of the present invention is to provide a temporarily emplacable device for maintaining patency while providing protection from enboli in blood vessels.

It is yet another object of the present invention to provide a device which can be emplaced through the superior or inferior vena cava, in a relatively simple procedure, during the course of which the device may be readily repositioned until optimally located in the vessel, and then positively fixed in that location for the desired, medically appropriate period.

A further object of the present invention is to provide a device which can be steered through the vena cava under appropriate imaging techniques.

Still a further object of the present invention is to provide an emboli filter which, when emplaced, remains centered, and even if tilted, will not allow significant escape of emboli or thrombi earlier collected in the trap.

A further important object of the present invention is to provide an emboli trap for emplacement in a blood vessel which can be permanently emplaced but which also can be readily removed after six weeks to six months or more, in order to open up complete flow through the vessel.

Another object of the present invention is to provide an emboli trap for placement in blood vessels which is neither subject to occlusion while emplaced, nor to embolization of trapped blood or release of attached emboli into the bloodstream upon removal from the vessel.

A still further object of the invention is provide a trap which is compliant and comfortable to the vessel wall, preventing either puncture or trauma of the vessel wall and the creation of potential sites for emboli formation and maintaining contact with the vessel wall as it dilates and contracts with vessel lumen alterations.

Another object of the present invention is provide an emboli trap with a member which maintains the trap in its desired location for as long as required, while permitting direct introduction of fluids to the region of the trap for purposes of venography and lysis of trapped emboli or thrombi.

A yet further object of the present invention is to provide a method for trapping emboli and preventing occlusion of blood vessels for as long as medically required, without damaging vessel walls or producing embolization of trapped blood or release of attached emboli upon removal of the device.

A still further object of the present invention is to provide a method for emplacing or removing a vena cava filter in which the emplacement and removal process is facilitated by the introduction of a contrast medium through the device into the vessel during the emplacement or removal process.

The present invention is therefore directed to a device for providing protection from emboli and for preventing occlusion of a blood vessel which includes a trap for filtering out emboli passing through the vessel while maintaining patency. The trap, even when open in the vessel, may again be moved within the vessel until located at the desired position.

The trap may comprise a plurality of resilient arms which, when unconfined, describe a generally conical surface. The arms are joined at their proximal ends to form the vertex of the generally conical surface. In an important embodiment, the arms include coil springs and in a particularly preferred embodiment, the arms include coil springs coated with a thromboresistant material such as urethane or silicone rubber.

The device further includes a hollow, longitudinally stable stem, affixed to the trap at the vertex for maintaining the trap in a desired location in the blood vessel. The stem has a lumen opening at its proximal end and adjacnet its point of affixation to the trap. This permits direct introduction of fluids to the region of the trap for purposes of venography and lysis of trapped emboli or thrombi. The stem may comprise a coil spring which preferably is coated with a thromboresistant material such as urethane or silicone rubber. An obturator is maintained in the lumen of the stem when the lumen is not in use to prevent stagnant blood from accumulating in the lumen and forming a potentially dangerous thrombus.

The invention also includes an introducer/remover apparatus and a method for providing protection from emboli and prevention of occlusion of a blood vessel involving the application of the trap and stem just described. Finally, the invention comprises a sterile kit including all of the elements necessary to carry out the method of the invention.

BRIEF DESCRIPTION OF THE DRAWINGS

The features of the invention which are believed to be novel are set forth with particularity in the appended claims. The invention, together with its objects and advantages, may be best understood by reference to the following description, taken in conjunction with the accompanying drawings, in which like reference numerals identify like elements in the several figures and in which:

FIG. 1 is an elevation view of a filter constructed in accordance with the teaching of the prior art, as represented by U.S. Pat. No. 3,952,747, showing the filter described there positioned in a blood vessel, such as the vena cava, with the blood vessel depicted in section;

FIG. 2 is an elevation view of a trap constructed in accordance with the present invention;

FIG. 3 is an elevation view of another trap constructed in accordance with the present invention, in which the resilient arms of the trap are spring coils;

FIG. 3A is an enlarged fragmentary view of the trap of FIG. 3 showing an obturator in place within the lumen of the trap stem;

FIG. 4 is an elevation view of yet another trap constructed in accordance with the present invention, in which the resilient arms of the trap form coaxial, generally conical surfaces;

FIG. 5 is an elevation view of the trap of FIG. 2 positioned in an introducer/remover apparatus of the present invention;

FIG. 5A is an enlarged fragmentary view of the mating threaded ends of the trap stem and stem extension taken at A in FIG. 5;

FIG. 5B is an enlarged view of an open cell silicone cuff including a threaded portion for mating with the stem extension of FIG. 5A;

FIG. 6 is a fragmentary schematic view of portions of the circulatory system of the human body, including the exterior jugular vein, illustrating the method of emplacing the trap of the present invention;

FIG. 7 is an elevation view of the introducer/remover apparatus of FIG. 5 in which the introducer catheter sheath is placed under tension is faciliate "steering" of the trap in the blood vessels;

FIG. 7A is an enlarged fragmentary view in cross-section of the distal end of the apparatus of FIG. 7 showing the trap contained within a sleeve seated against a lip at the top of the sleeve;

FIGS. 8A-8D are elevation views of the trap and distal end of the introducer remover apparatus illustrating the release of the trap of the present invention into the vena cava, just below the renal veins.

DESCRIPTION OF THE PREFERRED EMBODIMENT

Figure 9:
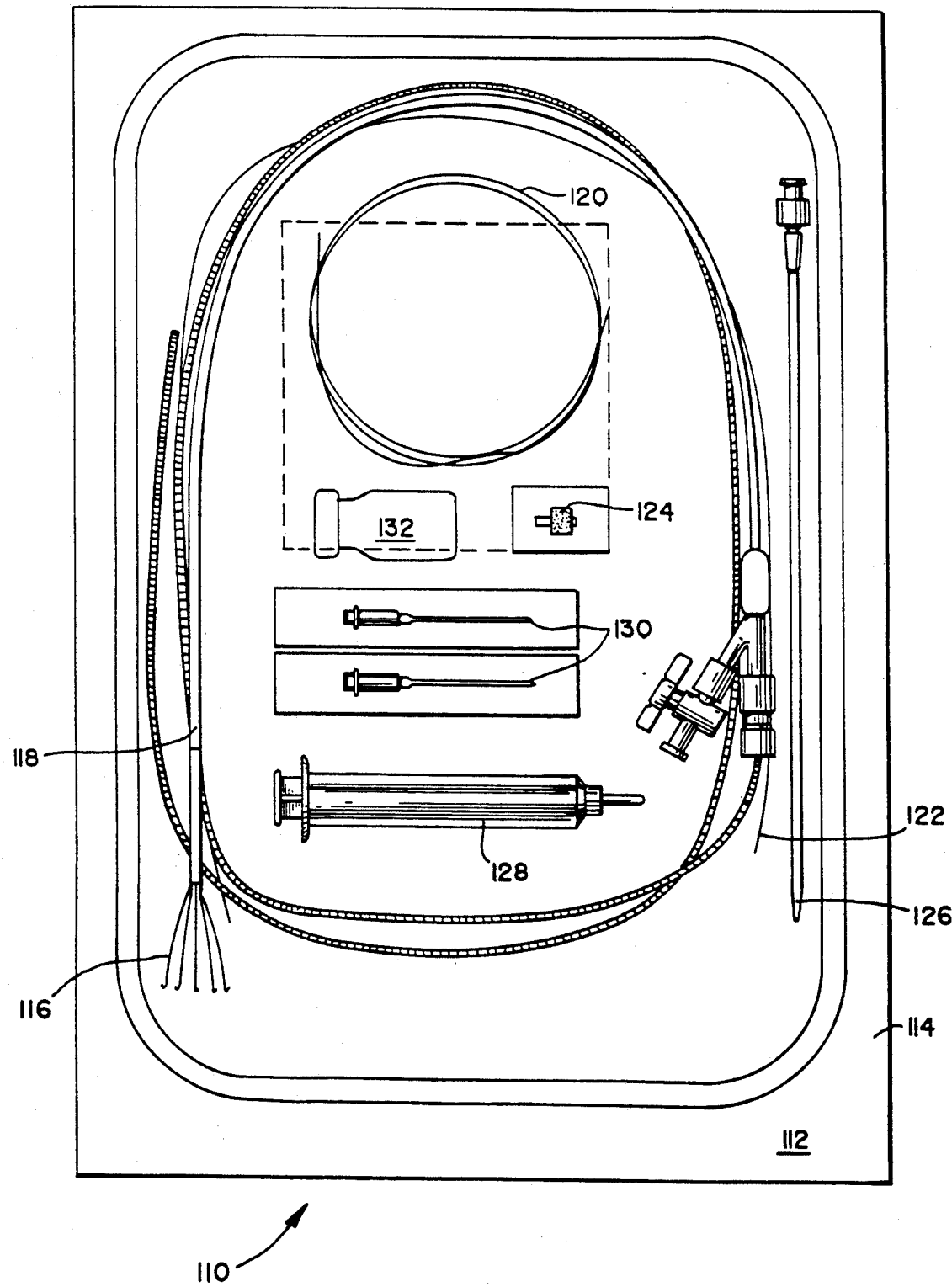
FIG. 9 is a top view of a kit in accordance with the present invention.

While the invention is described below in connection with the placement and utilization of a trap in the vena cava, the invention is not intended to be limited to this embodiment, but rather may be used in any blood vessel in which it is important to trap and remove or destroy emboli or thrombi.

Turning now to FIG. 2, a conformable, compliant trap 30 in accordance with the present invention is depicted. The trap is characterized as conformable and compliant because, in contrast to the rigid filters of the prior art, this trap is designed to yield elastically and thereby continuously adapt to the vessel physiology. Trap 30 thus comprises a plurality of stainless steel resilient arms 32A-32F. Each of the arms has a ball 34 at its tip to prevent the arms from impaling the wall of the vena cava in which the trap is to be positioned, which could not only damage the vessel but would also interfere with the conformability of the trap.

Resilient arms 32A-32F are welded and mechanically swaged at their proximal ends to a rigid collar 38 to form an open vertex 40 of the conical surface described by the arms. While six arms are illustrated as presently being preferred, from three arms to a number far in excess of six could be used.

Arms 32A-32F are resilient stainless steel wires. Resilient wires made of other metals or rods made of plastic or other materials could also be used. The flexibility of the arms makes the trap itself compliant and conformable to the contours of the architecture of the vena cava or other blood vessel in which it is emplaced. Indeed, the conformable, compliant nature of the arms also permits the filter to expand and contract to maintain contact with the vessel wall as it dilates and contracts with vessel lumen alterations. In one preferred embodiment, where stainless steel wires are used, the wires are of a diameter of from about 0.008 to 0.018 inches and have a tensile strength in the range of about 280,000 to 320,000 psi.

Another preferred form of the compliant, conformable trap of the invention is depicted at 50 in FIG. 3. The resilient arms in this figure include resilient wires 52 and closely would coil springs 54 which are welded and mechanically swaged to the wires. In one preferred embodiment, the coil springs may be wound of stainless steel wire having a diameter of from about 0.008 to 0.018 inches. The spring arms will, of course, be more flexible than the wire arms of FIG. 2, producing a more conformable and compliant trap. Thus, the springs, which includes balls 56 at their distal tips to prevent puncture of the vessel wall, further facilitate emplacement and minimize potential damage to the vessel wall.

As depicted in FIG. 4, in another preferred form of the compliant, conformable trap of the invention, 57, there are two coaxial generally conical surfaces described by arms 58A-F and 59A-F. Arms 58A-F and 59A-F are welded and mechanically swaged at their proximal ends to a rigid collar 61 to form an open vertex as in traps 30 (FIG. 2) and 50 (FIG. 3). Naturally, more than two coaxial generally conical coaxial surfaces can be employed in this embodiment of the invention.

The trap of the invention may be coated with an elastomeric material to further reduce potential damage to the vessel wall and further to avoid damage to the blood flowing through the vessel. Preferred elastomeric materials include urethane and silicone rubber, both of which are relatively thromboresistant as well.

A flexible, longitudinally stable stem 60 is permanently affixed to collar 38 at the vertex of trap 30 (FIG. 2), trap 50 (FIG. 3) and trap 57 (FIG. 4). The stem has a lumen 62 opening into the vertex at its distal end. Stem 60 is chosen to be of a length sufficient to reach from the intended position of the filter in the body to the outside of the body for attachment at an externally accessible point, as discussed in greater detail below, The stem, once attached to the body, keeps the trap centered in the vessel.

In FIG. 3A, an enlarged fragmentary view of trap 50 of FIG. 3 is shown with an obturator 64 filling the stem lumen to prevent stagnant blood from accumulating in the lumen and forming potentially dangerous emboli.

Stem 60 preferably comprises a tightly wound spring 66 covered with a flexible sheath 68. Useful materials for the sheath include urethane and silicone rubber. Futhermore, it is preferred that the lumen of the stem also be coated with a resilient, thromboresistant material such as silicone rubber or urethane.

Emplacement of the trap may be performed using introducer/remover apparatus 70 of FIG. 5. The introducer/remover apparatus 70 comprises an outer flexible catheter sheath 72, having a rigid sleeve 74 at its distal end and a control and treatment housing 76 at its proximal end. Control and treatment housing 76 includes seal and lock 78, flush port 80 and stopcock 82. Outer flexible catheter sheath 72 of the introducer apparatus 70 is broken away at A to show the proximal end 90 of the stem spaced from the mating distal end of stem extension 92. As seen in greater detail in the enlarged view of FIG. 5A, the proximal end of trap stem 90 is threaded at 94 to receive trap extension stem 92 having mating threaded end 96.

In preparation for emplacing the trap, it is first assembled into the introducer apparatus by attaching trap stem 60 to extension stem 92 and passing the stem extension and stem from rigid sleeve 74 up through catheter sheath 72, so that the proximal end of stem extension 92 protrudes from the introducer apparatus beyond lock 78.

The trap extension stem is then pulled upwardly to draw the trap into sleeve 74, which encompasses the arms of the trap, and lock 78 is tightened to hold the stem and trap firmly in place. The compliance of the arms permits the trap to be readily drawn into a small diameter sleeve, which facilitates introduction of the trap into the blood vessel. As seen in FIG. 7A, the top of the trap seats against a lip 99 at the top of sleeve 74. Pulling further on stem extension 92 will compress catheter sheath 72 causing it to bend and turning control and treatment housing 76 will cause the sheath to rotate, permitting the introducer/remover apparatus to be steered or directed within the blood vessel.

Finally, stopcock 82 is opened and the entire introducer apparatus is flushed with a heparinized saline solution introduced through port 80 and then closing stopcock 82 to prevent air from entering the system.

Turning now to FIG. 6, the exterior jugular vein 100 is located and either surgically exposed or reached percutaneously as a needle (not shown) is inserted into the vein with the patient on the x-ray table under local anesthesia. A radiopaque guidewire 98 is then passed through the needle into the vein to the selected site in the inferior vena cava while being viewed under fluoroscopy. Alternatively, the guidewire may be passed into the subclavian or the femoral arteries and into the inferior vena cava.

Introducer/remover apparatus 70 is then passed over the guidewire which enters the compressed filter in sleeve 74 and passes through the vertex of the filter and the lumen in the filter stem and stem extension as the introducer apparatus is advanced along the guidewire into the jugular vein 100. After positioning the device in the inferior vena cava the guidewire is removed.

Although an inferior venacavogram is typically required to be performed by way of a femoral vein approach prior to any jugular vein cutdown using prior art devices, this is not necessary using the trap of the present invention. The renal veins 102 rather may be located by passing a marking fluid through the apparatus to identify the renal veins.

When, as illustrated in FIG. 8A, sleeve 74 reaches just below the renal veins 102, the filter stem extension is released at lock 78 (FIG. 4) and the introducer/remover apparatus is drawn upwardly along the stem first releasing the trap as shown in FIGS. 8B and 8C and then entirely withdrawing the introducer/remover apparatus leaving the stem and trap positioned as shown in FIG. 8D.

Once the filter is in place at the desired location and the introducer/remover apparatus is removed, the stem extension, which is now outside of the body, is unscrewed from the stem. An obturator 68 is then inserted in the lumen of the stem 9 to completely fill the stem and prevent stagnant blood from accumulating in the lumen and forming potentially dangerous emboli. The positioning may be rechecked and, if necessary, the trap may be readily moved by retracting it back into the sleeve. An open cell silicone cuff 106, as depicted in FIG. 5B, is then screwed into the threaded proximal end of the stem and attached to the patient's skin adjacent the jugular entry point.

A follow-up venacavagram may be performed by simply removing the cuff and the obturator and passing the marker solution through lumen 62 in stem 60. Indeed, should it become necessary or desirable to inspect the condition of the trap as well as its placement at a future date, it is necessary only to uncover the proximal end of the stem lumen, remove the obturator and introduce the necessary marker solution for performing a cavagram.

Furthermore, lysis of any emboli or thrombi accumulating in the filter may be undertaken again by simply removing the obturator and passing a lysing agent through the lumen in the catheter. Alternatively, suction can be applied to the open lumen to withdraw clots from the trap and surrounding area.

When it becomes appropriate—typically within six weeks to six months after emplacement—the trap may be readily removed from the blood vessel. This is accomplished by simply releasing open-cell silicone cuff 106, unscrewing the cuff, removing obturator 64 and flushing a lysing agent through the stem lumen. The silicone cuff is then replaced by extension stem 92. Then, the introducer/remover apparatus is passed over the extension catheter to compress trap 30 in sleeve 74 and the stem is locked in place by tightening lock 78. The introducer apparatus along with the trap and stem are then withdrawn and the jugular vein is closed.

The present invention includes the provision of a sterile kit 110 particularly adapted for the practice of this invention. As best shown in FIG. 9, the sterile kit includes a sealed package such as a tray 112 and a clear plastic film pouch 114 defining a sterile interior. Positioned in the sterile interior of the package are a trap 116 including a stem and stem extension in accordance with the present invention, which is mounted in an introducer/remover apparatus 118. Also provided are guidewire 120, an obturator 122 and, a threaded foam cuff 124. The kit may also optionally include a dilator 126 for opening the jugular vein, a syringe 128, and two needles 130, one for injecting the anesthetic lidocaine in container 132 and one for finding the jugular vessel when the device is to be introduced percutaneously.

It is contemplated that the filter, the introducer/remover apparatus and the guidewire will be maintained in a sterile condition prior to packaging in the kit, and that the kit can be conveniently assembled under sterile conditions by positioning the parts to be contained therein on tray 112. Following assembly, the kit will remain sterile until pouch 114 is pierced or removed.

While particular embodiments of the invention have been shown and described, it will be obvious to those skilled in the art that various changes and modifications may be made therein without departing from the spirit and scope of the invention and, therefore, it is intended in the appended claims to cover all such changed and modifications which fall within the true spirit and scope of the invention.

What we claim is:

1. A vena cava filter for providing protection from potentially life threatening pulmonary emboli comprising:
    means, movable within the vessel, for trapping potentially life-threatening pulmonary emboli passing through the vessel while maintaining patency therein; and
    means, affixed to the trapping means, for both maintaining the trapping means in a desired location in the blood vessel and for introducing fluid to the region of the trapping means for purposes of lysis of the trapped emboli.

2. The vena cava filter device of claim 1 wherein the trapping means is conformable and compliant whereby it continuously adapts to the vessel physiology.

3. The vena cava filter of claim 1 wherein the trapping means comprises a plurality of resilient arms which, when unconfined, described a generally conical surface.

4. A vena cava filter of claim 3 wherein the resilient arms include means at their distal ends for preventing the arms for impaling the vessel walls.

5. The vena cava filter of claim 3 wherein the arms have rounded tips at their distal ends.

6. The vena cava filter of claim 3 wherein the trapping means comprises at least six arms of substantially equal lengths positioned generally symmetrically about a central axis.

7. The vena cava filter of claim 3 wherein the trapping means comprises at least two groups of resilient arms which when unconfined, describe at least two generally conical coaxial surfaces.

8. The vena cava filter of claim 3 wherein the arms are joined at their proximal ends to form the vertex of the conical surface, the maintaining and introducing means being permanently attached to the trapping means at the vertex.

9. The protection and prevention device of claim 3 wherein the arms are stainless wires of diameter from about 0.008 to 0.018 inches, having a tensile strength of about 280,000 to 320,000 psi.

10. The protection and prevention device of claim 3 wherein the arms include coil springs at their distal ends.

11. A device for providing protection from emboli and prevention of occlusion in the vena cava, comprising:
    conformable and complaint means for trapping emboli passing through the vessel while maintaining patency therein and continuously adapting to the vessel physiology comprising a plurality of resilient arms which, when unconfined, describe a generally conical surface, the arms including means at their distal ends for preventing the arms from impaling the blood vessel walls; and
    means, affixed to the trapping means, comprising a flexible, longitudinally stable member having a lumen along its length and a removable obturator in the lumen, the lumen opening both at its proximal end and at the point of affixation to the trapping means, for both maintaining the trapping means in a desired location in the blood vessel and for introducing fluid to the region of the trapping means upon removal of the obturator.

12. A method for providing protection from emboli and prevention of occlusion of a blood vessel in the body comprising
    placing in the vessel means for trapping emboli passing therethrough, the trapping means including means, affixed thereto, for both maintaining the trapping means in a desired location in the blood vessel and for introducing fluid to the region of the trapping means for purposes of lysis of the trapped emboli.

13. The method of claim 12 including the step of first introducing fluid to the region of the trapping means for purposes of lysis of the trapped emboli and thereafter removing the trapping means from the blood vessel.

14. A sterile kit for providing protection from emboli and prevention of occlusion of a blood vessel comprising:
    a sealed package, the interior of which is sterile;
    an apparatus comprising means for trapping emboli and preventing occlusion of a blood vessel in the body including a hollow stem affixed to the trapping and preventing means;
    a guidewire;

an introducer/remover apparatus;

an obturator; and means for attachment of the hollow stem to the body.

15. A device for providing protection from emboli and prevention of occlusion of a blood vessel, comprising a plurality of resilient arms which, when unconfined, describe a generally conical surface, said arms including coil springs at their distal ends; and means, affixed to the trapping means, for both maintaining the trapping means in a desired location in the blood vessel and for introducing fluid to the region of the trapping means for purpose of lysis of the trapped emboli.

16. The protection and prevention device of claim 15 wherein the coil springs are wound from stainless steel wire having a diameter of about 0.008 to 0.018 inches.

17. The protection and prevention device of claim 15 wherein the coil springs have balls at their distal tips.

18. The protection and prevention device of claim 15 wherein the coil springs are coated with a thromboresistant material.

19. The protection and prevention device of claim 15 wherein the trapping means is coated with a thromboresistant material.

20. The protection and prevention device of claim 15 wherein the maintaining and introducing means comprises a flexible, longitudinally stable member having a lumen along its length, the lumen opening both at its proximal end and at the point of affixation to the trapping means.

21. The protection and prevention device of claim 20 wherein the flexible, longitudinally stable member comprises a coil spring.

22. The protection and prevention device of claim 21 wherein the coil spring is sheathed with a thromboresistant material.

23. The protection and prevention device of claim 21 wherein the thromboresistant material is chosen from the group consisting of silicone rubber and urethane.

* * * * *

UNITED STATES PATENT AND TRADEMARK OFFICE
CERTIFICATE OF CORRECTION

PATENT NO. : 5,152,777
DATED : October 6, 1992
INVENTOR(S) : Edward M. Goldberg

It is certified that error appears in the above-identified patent and that said Letters Patent is hereby corrected as shown below:

Col. 1, line 15, "below" should be "hollow"

Col. 3, line 7, insert "filter" after "Greenfield"

Col. 4, line 43, insert "present" after "the"

Col 6, line 66, "would" should be "wound"

Claim 2, line 1, delete "device".

Signed and Sealed this

Twelfth Day of October, 1993

Attest:

BRUCE LEHMAN

Attesting Officer  Commissioner of Patents and Trademarks